(12) United States Patent
Crutchfield, III

(10) Patent No.: US 6,579,512 B2
(45) Date of Patent: Jun. 17, 2003

(54) TOPICAL STEROID SPRAY

(76) Inventor: Charles E. Crutchfield, III, 1383 Chatterton Rd., St. Paul, MN (US) 55123

(*) Notice: Subject to any disclaimer, the term of this patent is extended or adjusted under 35 U.S.C. 154(b) by 0 days.

(21) Appl. No.: 09/882,965

(22) Filed: Jun. 15, 2001

(65) Prior Publication Data

US 2003/0007929 A1 Jan. 9, 2003

(51) Int. Cl.[7] .............................. A61K 9/12; A61K 7/48
(52) U.S. Cl. ................. 424/43; 424/78.05; 128/200.14; 514/861; 514/871; 514/863; 514/887; 514/886
(58) Field of Search .................. 424/43, 401, 78.05; 514/171, 861, 863, 871, 887, 886; 128/200.14

(56) References Cited

U.S. PATENT DOCUMENTS 5,972,920 A    10/1999  Seidel
6,096,326 A  *  8/2000  Wikholm .................... 424/401

OTHER PUBLICATIONS

The Merck Index, Ninth Edithion, Merck & Co, Inc, 1976.*
Product information for Cormax 0.05% Cream (Clobetasol Propionate Cream USP), Jul., 1988 (2 pgs.).
Article entitled "The Effective Use of Topical Zinc Pyrithione in the Treatment of Psoriasis: A Report of Three Cases", vol. 5, No. 1, Jan./Feb. 1997, (pp. 21–24).
Product information entitled "Dermalogix Partners, Inc., The New #1 Psoriasis Treatment, Mirror Image of Skin Cap", vol. 7, No. 12, Dec. 1999 (2 pgs.).
NOVA Medical Laboratories' advertisement appearing in Cosmetic Dermatology, Dec., 1995 (2 pgs.).
Information entitled "Triamcinolone Acetonide Spray (Reformulated) in the Treatment of Topical Steroid–Responsive Dermatoses", Ronald Goldner, M.D. (pp. 659–661).
Product Information, Glaxo Wellcome (pp. 1277–1282).
Article entitled "The Journal of Investigative Dermatology", presented by Westwood Squibb (3 pgs.).
Dermatology Online Journal, vol. 3, No. 1, Mar. 1997 (8 pgs.).

* cited by examiner

Primary Examiner—Jose' G. Dees
Assistant Examiner—Mina Haghighatian
(74) Attorney, Agent, or Firm—Gerald E. Helget; Nelson R. Capes; Briggs and Morgan

(57) ABSTRACT

A pharmaceutical topical spray composition of corticosteroid, an alcohol, a propelant, and isopropyl myristate. A method for treating an inflammatory skin condition using the administration to the skin of a mammal of the pharmaceutical composition. The pharmaceutical composition is effective in the treatment of inflammatory skin conditions without the need for zinc pyrithione, undecylenic acid, or a detergent.

31 Claims, No Drawings

TOPICAL STEROID SPRAY

BACKGROUND OF THE INVENTION

The present invention relates to a pharmaceutical composition of the treatment of inflammatory skin conditions, and a therapeutic method for treating inflammatory skin conditions using the pharmaceutical composition.

Topical corticosteroids are a powerful tool for treating skin disease. Understanding the correct use of these agents will result in the successful management of a variety of skin problems. There are many products available, and new ones appear almost monthly. Pharmaceutical companies have responded to the great demand for these agents with an increasing number of products, but all of these preparations have basically the same antiinflamatory properties. They differ only in strength, base and price.

The antiinflammatory properties of topical corticosteroids result in part from their ability to induce vasoconstriction of the small blood vessels in the upper dermis. This property is used in an assay procedure to determine the strength of each new product. These products are subsequently tabulated in seven groups, with group I the strongest and group VII the weakest (see the Formulary below).

| Group No. | Generic Name |
| --- | --- |
| I | Clobetasol propionate |
| II | Fluocinonide |
| III | Triamcinolone acetonide |
| IV | Fluocinolone acetonide |
| V | Hydrocortisone valerate |
| VI | Desonide |
| VII | Hydrocortisone |

The treatment recommends topical steroids by group number rather than by generic or brand name because the agents in each group are essentially equivalent in strength. When a new topical corticosteroid appears on the market, ask to which group it belongs and add it to the list in the Formulary.

Guidelines for choosing the appropriate strength of topical steroid are presented in the chart below.

| SUGGESTED STRENGTH OF TOPICAL STEROIDS TO INITIATE TREATMENT* | | |
| --- | --- | --- |
| GROUPS I–II | GROUPS III–V | GROUPS VI–VII |
| Psoriasis | Atopic dermatitis | Dermatitis (eyelids) |
| Lichen planus | Nummular eczema | Dermatitis (diaper area) |
| Discoid lupus† | Asteatotic eczema | Mild dermatitis (face) |
| Severe hand eczema | Stasis dermatitis | Mild anal inflammation |
| Poison ivy (severe) | Seborrheid dermatitis | Mild intertrigo |
| Lichen simplex chronicus | Lichen sclerosis et atrophicus (vulva) | |
| Hyperkeratotic eczema | Intertrigo (brief course) | |
| Chapped feet | Tinea (brief course to control inflammation) | |
| Lichen sclerosis et atrophicus (skin) | Scabies (after scabicide) | |
| Alopecia areata | Intertrigo (severe cases) | |
| Nummular eczema (severe) | Anal inflammation (severe cases) | |
| Atopic dermatitis (resistant adult cases) | Severe dermatitis (face) | |

*Stop treatment, change to less potent agent, or use intermittent treatment once inflammation is controlled.
†Use on the face may be justified.

The best results are obtained when preparations of adequate strength are used for a specified length of time. Weaker, "safer" strengths often fail to provide adequate control. Patients who do not respond after 1 to 4 weeks of treatment should be reevaluated.

Additionally, topical preparations of the steroid clobetasol propionate are indicated for the relief of the inflammatory and pruritic manifestations of cortico-steroid-responsive dermatosis. See, for example, Maloney, et.al., "Clobetasol Propionate Emollient 0.05% in the Treatment of Atopic Dermatitis", International J. of Dermatology, 1998, 37, 128–144.

In the past, it has been found that clobetasol propionate is most effective in the treating of inflammatory skin conditions when combined with zinc pyrithione and undecylenic acid. For example, Seidel (U.S. Pat. No. 5,972,920) discloses the use of clobetasol propionate in combination with either zinc pyrithione, undecylenic acid, or both. Applicant Crutchfield also noted the requirement for zinc pyrithione in Crutchfield, et.al., "The Effective Use of Topical Zinc Pyrithione in the Treatment of Psoriasis: a Report of Three Cases", J. Geriatr. Dermatol. 1997; 5(1):21–4.

Surprisingly, the applicants have found that zinc pyrithione and undecylenic acid are not necessary for the optimal effectiveness of clobetasol propionate.

Studies have also indicated that some sort of surfactant, such as sodium lauryl sulfate, is necessary for the optimal effectiveness of clobetasol propionate, whether alone or combined with zinc pyrithione and undecylenic acid. Again, Seidel '920 discloses the use of an anionic surfactant (sodium lauryl sulfate) in conjunction with clobetasol propionate, zinc pyrithione, and undecylenic acid.

Surprisingly, the applicants have found that no surfactant is necessary for the optimal effectiveness of clobetasol propionate.

Applicants have also found that the composition is most effective and easily tolerated by patients when administered in a spray form by means of a propellant. In contrast, Seidel '920 teaches away from the use of a spray as being highly evaporative and producing a painful freezing sensation to the skin and that some propellants are explosive.

SUMMARY OF THE INVENTION

A pharmaceutical topical spray composition of corticosteroid, an alcohol, a propelant, and isopropyl myristate. A method for treating an inflammatory skin condition using the administration to the skin of a mammal of the pharmaceutical composition. The pharmaceutical composition is effective in the treatment of inflammatory skin conditions without the need for zinc pyrithione, undecylenic acid, or a detergent.

DETAILED DESCRIPTION OF THE PREFERRED EMBODIMENT

A pharmaceutical composition for the treatment of inflammatory skin conditions consists essentially of clobetasol propionate, an alcohol, a propellant, and isopropyl myristate, suitable for topical administration. The composition is suitably carried in a aerosol can with a nozzle. Applicants have found that no other active ingredients are necessary for the optimal pharmaceutical action of clobetasol propionate.

Preferably, the clobetasol propionate is present in about 0.01 to 10% (%w/w). More preferably, the clobetasol propionate is present in about 0.01% to 1% (%w/w). Most preferably, the clobetasol propionate is present in the amount of 0.05% (%w/w). Any of the above corticosteroids may be used in this spray formulary.

Any number of alcohols can be used as a solvent in the preparation, such as methanol, ethanol, propanol, isopropanol, butanol, or isobutanol. However, Applicants have found that denatured ethanol (SDA-40 200 proof) is a suitable and effective alcohol to use in the composition. Most preferably, the ethanol, is present in the amount of 37.73% (%w/w). However, a range of 27% (%w/w) to 47% (%w/w) may be used while a narrower range of 32% (%w/w) to 42% (%w/w) is more suitable.

The composition also contains isopropyl myristate as an emollient oil or carrier most preferably in the amount of 37.72% (%w/w). However, a range of 27% (%w/w) to 47% (%w/w) may be used while a narrower range of 32% (%w/w) to 42% (%w/w) is more suitable.

An inactive ingredient, but one of importance in delivery of the composition to the skin, is a propellant. Any propellant conventionally used in the delivery of aerosol sprays may be used. Most preferably, an amount of 24.51% (%w/w) of AK6 propane/butane blend is in the composition. However, a range of 20% (%w/w) to 30% (%w/w) may also be suitable.

Importantly, the composition does not contain either zinc pyrithione or undecylenic acid.

A therapeutic method for treating an inflammatory skin condition comprises administering the above composition to the skin of a mammal in need of such therapy.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A therapeutic method for treating an inflammatory skin condition comprising administering by spray to the skin of a mammal in need of such therapy, an effective amount of a pharmaceutical composition consisting essentially of clobetasol proprionate and isopropyl myristate.

2. The therapeutic method of claim 1, wherein the clobetasol proprionate is present in about 0.01 to 10% (%w/w).

3. The therapeutic method of claim 1, wherein the clobetasol propionate is present in about 0.01 to 1% (%w/w).

4. The therapeutic method of claim 1, wherein the clobetasol propionate is present in about 0.05% (%w/w).

5. The therapeutic method of claim 1, wherein the isopropyl myristate is present in about 38% (%w/w).

6. The therapeutic method of claim 1, wherein the isopropyl myristate is present in arrange of 27% (w/w) to 47% (%w/w).

7. The therapeutic method of claim 1, wherein the isopropyl myristate is present in a range of 32% (w/w) to 42% (%w/w).

8. The therapeutic method of claim 1, wherein the inflammatory skin condition is psoriasis, atopic dermatitis, eczema, lupus, poison ivy, scabies, severe skin inflammation, dermatitis, lichen , or papulolsquamous.

9. The therapeutic method of claim 1, wherein the pharmaceutical composition is delivered in spray form by means of a propellant comprising 25% (%w/w) of propane/butane blend.

10. The therapeutic method of claim 1, wherein the pharmaceutical composition is delivered in spray form by means of a propellant in a range of 20% (%w/w) to 30% (%w/w).

11. The therapeutic method of claim 1, wherein the administration is performed in the absence of zinc pyrithione.

12. The therapeutic method of claim 6, wherein the administration is performed in the absence of undecylinic acid.

13. A pharmaceutical topical spray composition consisting essentially of clobetasol propionate and isopropyl myristate as a carrier.

14. The pharmaceutical composition of claim 13, wherein the clobetasol propionate is present in about 0.01 to 10% (%w/w).

15. The pharmaceutical composition of claim 13, wherein the clobetasol propionate is present in about 0.01 to 1% (%w/w).

16. The pharmaceutical composition of claim 13, wherein the clobetasol propionate is present in about 0.05% (%w/w).

17. The pharmaceutical composition of claim 13, wherein the isopropyl myristate is present in about 38% (%w/w).

18. The pharmaceutical composition of claim 13, wherein the isopropyl myristate is present in a range of 27% (%w/w) to 47% (%w/w).

19. The pharmaceutical composition of claim 13, wherein the isopropyl myristate is present in a range of 32% (%w/w) to 42% (%w/w).

20. The pharmaceutical composition of claim 13, wherein the composition is delivered in spray form by means of a propellant comprising 25% (%w/w) of a propane/butane blend.

21. The pharmaceutical composition of claim 13, wherein said composition is free of zinc pyrithione and undecylenic acid.

22. A therapeutic method for treating an inflammatory skin condition comprising administering by spray to the skin of a mammal in need of such therapy, an effective amount of a pharmaceutical composition consisting essentially of corticosteroid and isopropyl myristate.

23. The therapeutic method of claim 22, wherein the corticosteroid is present in about 0.01 to 10% (%w/w) and chosen from a group comprising clobetasol propionate, fluocinonide, triamcinolone acetonide, fluocinolene acetonide, hydrocortisone valerate, desonide, and hydrocortisone.

24. The therapeutic method of claim 22, wherein the corticosteroid is present in about 0.01 to 1% (%w/w) and chosen from a group comprising clobetasol propionate, fluocinonide, triamcinolone acetonide, fluocinolene acetonide, hydrocortisone valerate, desonide, and hydrocortisone.

25. The therapeutic method of claim 22, wherein the corticosteroid is present in about 0.05% (%w/w) and chosen from a group comprising clobetasol propionate, fluocinonide, triamcinolone acetonide, fluocinolene acetonide, hydrocortisone valerate, desonide, and hydrocortisone.

26. The therapeutic method of claim 22, wherein the isopropyl myristate is present in about 38% (%w/w).

27. The therapeutic method of claim 22, wherein the isopropyl myristate is present in a range of 27% (w/w) to 47% (%w/w).

28. The therapeutic method of claim 22, wherein the isopropyl myristate is present in a range of 32% (w/w) to 42% (%w/w).

29. The therapeutic method of claim 22, wherein the inflammatory skin condition is psoriasis, atopic dermatitis, dermatitis, lichen planus, or papulosquamous.

30. The therapeutic method of claim 22, wherein the pharmaceutical composition is delivered in spray form by means of a propellant comprising 25% (%w/w) of propane/butane blend.

31. The therapeutic method of claim 22, wherein the administration is performed in the absence of zinc pyrithione.

* * * * *